United States Patent [19]

Biere et al.

[11] Patent Number: 4,473,560

[45] Date of Patent: Sep. 25, 1984

[54] DIPHOSPHONIC ACID DERIVATIVES AND PHARMACEUTICAL PREPARATIONS CONTAINING THEM

[75] Inventors: Helmut Biere; Clemens Rufer, both of Berlin; Irmgard Boettcher, Basel, all of Fed. Rep. of Germany

[73] Assignee: Schering Aktiengesellschaft, Berlin and Bergkamen, Fed. Rep. of Germany

[21] Appl. No.: 461,412

[22] Filed: Jan. 27, 1983

[30] Foreign Application Priority Data

Jan. 27, 1982 [DE] Fed. Rep. of Germany ....... 3203309
Jul. 5, 1982 [DE] Fed. Rep. of Germany ....... 3225468

[51] Int. Cl.³ ....................... A61K 31/67; A61K 31/66
[52] U.S. Cl. ............................ 424/202; 424/204; 260/502.4 P; 260/502.4 A; 260/932; 549/6
[58] Field of Search ............. 260/502.4 P, 502.4 A, 260/932; 549/6; 424/202, 204

[56] References Cited

U.S. PATENT DOCUMENTS 3,664,975 5/1972 Kerst ........................... 260/502.4 P 4,069,246 1/1978 Blum ........................... 260/502.4 P Primary Examiner—Alan Siegel
Attorney, Agent, or Firm—Millen & White

[57] ABSTRACT

Compounds of the formula

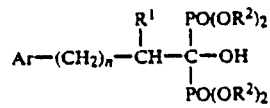

wherein
n is 0, 1, or 2;
R¹ is hydrogen or alkyl of 1–4 carbon atoms;
R² is hydrogen, an alkali metal atom, an alkaline earth metal atom, or alkyl of 1–4 carbon atoms; and
Ar is phenyl; phenyl substituted by fluorine, chlorine, alkyl of 1–4 carbon atoms, or alkoxy of 1–4 carbon atoms; naphthyl; biphenyl; or thienyl;
or when R² is H, a physiologically acceptable salt thereof with an organic base
have valuable antiinflammatory properties.

21 Claims, No Drawings

DIPHOSPHONIC ACID DERIVATIVES AND PHARMACEUTICAL PREPARATIONS CONTAINING THEM

The present invention relates to diphosphonic acid derivatives and to pharmaceutical preparations containing them.

SUMMARY OF THE INVENTION

It is an object of the invention to provide new compounds having valuable pharmacological properties.

Upon further study of the specification and appended claims, further objects and advantages of this invention will become apparent to those skilled in the art.

These objects have been achieved by providing diphosphonic acid derivatives of Formula I

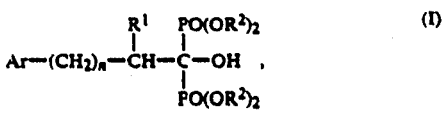

wherein
n is 0, 1, or 2;
$R^1$ is hydrogen or alkyl of 1–4 carbon atoms;
$R^2$ is hydrogen, an alkali metal, and alkaline earth metal atom, or alkyl of 1-4 carbon atoms, and
Ar is phenyl optionally substituted by fluorine atom(s), chlorine atom(s), alkyl group(s) of 1–4 carbon atoms, or alkoxy group(s) of 1–4 carbon atoms; naphthyl; biphenyl; or thienyl;
or physiologically acceptable salts thereof with an organic base.

DETAILED DESCRIPTION

The compounds of this invention, in contrast to the carboxylic acids of Formula II

wherein the substituents are as defined for formula (I), possess a pronounced antiinflammatory and antiarthritic activity. Moreover, they are distinguished in that they are capable, inter alia, of affecting the productive and destructive power of the bone cells (osteoblasts/osteoclasts) in such a way that curative effects can clearly be proven to exist in rats with induced arthritis.

This antiarthritic activity of the compounds of this invention forms the basis for therapy of rheumatoid arthritis, osteoarthritis, ankylosing spondylitis, and other related diseases, especially of the collagen and the skeletal system (e.g., osteoporosis, Paget's disease, etc.). Morover, the phosphonates can be utilized in a therapeutically meaningful fashion as good complexing agents for calcium in all cases where a distrubed calcium metabolism has been recognized as cause for a disease, for example in cardiovascular disorders, ectopic calcifications, etc.

The compounds can be employed in the form of their full alkyl esters or di-monoesters (half esters), but preferably in the form of the free phosphonic acids and/or their physiologically compatible salts with alkali or alkaline earth hydroxides or with compatible organic bases, e.g. sodium hydroxide, potassium hydroxide, calcium hydroxide, piperazine or methylglucamine.

Suitable alkyl groups in formula I include methyl, ethyl, the propyls and the butyls; suitable alkoxy groups include the corresponding alkoxy groups. Suitable cations are Na, K, Ca, Ba, Sr, Mg, etc. All points of attachment of naphthyl, biphenyl and thienyl are possible.

Suitable galenic formulations for enteral or parenteral administration include capsules, tablets, dragees, suppositories, and also injection solutions and dermal preparations. Also, local application is possible for the treatment of dermal or systemic diseases.

The medical specialties are prepared in the usual way by converting the active agents into the desired forms of application with suitable additives, e.g., solutions, lotions, ointments, creams, or plasters. In the thus-formulated medicines, the concentration of active compound is dependent on the type of application. In the case of lotions and ointments, an active agent concentration of 0.1% to 10% is preferably employed. Administration is as conventional with such topical formulations, e.g., as with a hydrocortisone cream.

The novel corticoids are also suitable furthermore in the form of capsules, tablets, or dragees, etc., containing preferably 10–500 mg of active agent and being administrable orally (e.g., at daily dosages of 1-50 mg/kg), e.g., analogously to the known agent indometacine or naproxene.

Conventional excipients are pharmaceutically acceptable organic or inorganic carrier substances suitable for parenteral, enteral or topical application to mammals, including humans, which do not deleteriously react with the active compounds. Suitable pharmaceutically acceptable carriers include but are not limited to water, salt solutions, alcohols, gum arabic, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy-methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are injectable sterile solutions, preferably oily or aqueous solutions, as well as suspensions, emulsions, or implants, including suppositories. Ampoules are convenient unit dosages.

For enteral application, particularly suitable are tablets, dragees, suppositories or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

Dosages for a given host for a given indication can be determined, e.g., by customary comparison of the activities of the subject compound and of a known agent by means of an appropriate, conventional pharmacological protocol.

The diphosphonic acid derivatives can be prepared according to methods which are well known to those skilled in the art and disclosed, e.g., in Houben-Weyl, "Methoden der organischen Chemie" (Methods of Organic Chemistry) Georg Thieme publishers, Stuttgart, 4th edition (1963) XII/1: 453 et seq. whose disclosures are incorporated by reference herein; such methods are represented in the schematic below wherein an acyl phosphonate of Formula II

Ar—(CH$_2$)$_n$—CHR$^1$—CO—PO(OR$^2$)$_2$      (II)

wherein Ar, n, R$^1$ and R$^2$ are as defined for formula I, is reacted in the presence of a base with a dialkyl phosphite of formula III

HPO(OR$^2$)$_2$      (III)

wherein R$^2$ is as defined above, and optionally saponifying the thus-formed esters, and optionally converting the acids into the salts thereof.

SCHEME

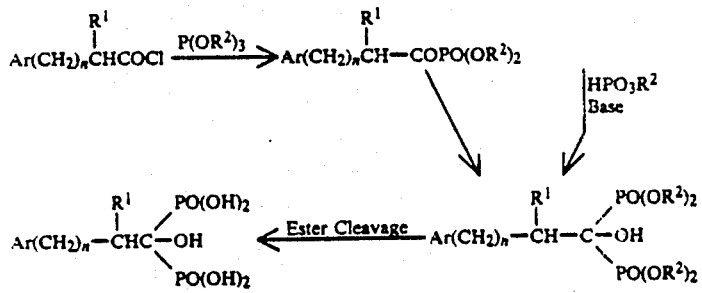

Examples of suitable bases for conducting the process of this invention include secondary amines, e.g., diethylamine, dipropylamine, diisopropylamine, morpholine, or piperidine. The reaction is conducted in inert organic solvents, e.g., ethers (e.g. diethyl ether, diisopropyl ether, dioxane, tetrahydrofuran) or chlorinated hydrocarbons (e.g. dichloromethane, tetrachloroethane, chloroform, or carbon tetrachloride).

The optionally subsequently effected saponification of the esters can take place with mineral acids (e.g. semiconcentrated hydrochloric acid or sulfuric acid). The cleavage reaction occurs in an especially gentle fashion in an inert solvent (for example one of the above-mentioned chlorinated hydrocarbons) with trimethylsilyl iodide. For the salt formation, the free acids are reacted as usual conventionally with the corresponding bases.

The starting compounds of Formula II required for the process of this invention can be prepared conventionally from the corresponding acid chlorides by reaction with dialkyl phosphites of Formula III. The acid chlorides are all known or fully conventionally preparable.

These syntheses illustrated in the schematic chart will be explained in greater detail in the following practical examples with reference to typical representatives.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following example(s), all temperatures are set forth uncorrected in degrees Celsius; unless otherwise indicated, all parts and percentages are by weight.

EXAMPLE 1

At 0° C., a solution of 6.9 g of trimethyl phosphite in 20 ml of diethyl ether is added dropwise under agitation to a solution of 9.5 g of 4-chlorophenylacetic acid chloride in 50 ml of diethyl ether. The mixture is agitated for another 90 minutes, the thus-obtained precipitate is vacuum-filtered, yielding 9.3 g (71%) of 2-(4-chlorophenyl)-1-hydroxyethenephosphonic acid dimethyl ester, mp 89°–92° C.

At 0° C., a solution of 3.95 g of 2-(4-chlorophenyl)-1-hydroxyethenephosphonic acid dimethyl ester in 10 ml of dichloromethane and 15 ml of diethyl ether is added dropwise to a solution of 1.5 g of dimethyl phosphite and 0.114 g of diethylamine in 50 ml of diethyl ether. The mixture is stirred for 60 hours at 0° C., the thus-separated product is vacuum-filtered and washed with diethyl ether, thus obtaining 4.0 g (71.6%) of 2-(4-chlorophenyl)-1-hydroxyethane-1,1-bis(phosphonic acid dimethyl ester), mp 123° C.

EXAMPLE 2

Under nitrogen, 8.7 g of iodotrimethylsilane is added dropwise at 0° C. to a suspension of 3.35 g of 2-(4-chlorophenyl)-1-hydroxyethane-1,1-bis(phosphonic acid dimethyl ester) in 30 ml of carbon tetrachloride. The mixture is allowed to stand for 4 hours, concentrated, the residue hydrolyzed with acetone/water, and recrystallized from acetonitrile/diethyl ether, yielding 2.45 g of 2-(4-chlorophenyl)-1-hydroxyethane-1,1-diphosphonic acid, mp 219° C.

EXAMPLE 3

3.35 g of 2-(4-chlorophenyl)-1-hydroxyethene-1,1-bis(phosphonic acid dimethyl ester) is heated in 20 ml of concentrated hydrochloric acid for 2 hours on a steam bath. The mixture is then allowed to cool, diluted with water, the thus-separated product is vacuum-filtered, dried, recrystallized from acetonitrile/diethyl ether, and the product is 2.21 g (78%) of 2-(4-chlorophenyl)-1-hydroxyethane-1,1-diphosphonic acid, mp 219° C.

EXAMPLE 4

4-Biphenylacetic acid chloride is reacted as described in Example 1, yielding 2-(4-biphenyl)-1-hydroxyethene-1-phosphonic acid dimethyl ester, mp 156°–157° C. (from toluene).

The thus-obtained product is reacted as set forth in Example 1, thus producing 2-(4-biphenyl)-1-hydroxyethane-1,1-bis(phosphonic acid dimethyl ester), mp 147°–149° C. (from carbon tetrachloride).

EXAMPLE 5

4-Methoxyphenylacetic acid chloride is reacted as disclosed in Example 1, thus obtaining 2-(4-methoxyphenyl)-1-hydroxyethene-1-phosphonic acid dimethyl ester, mp 135°–137° C. (from diethyl ether).

The resultant product is reacted analogously to Example 1, thus producing 2-(4-methoxyphenyl)-1-hydroxyethane-1,1-bis(phosphonic acid dimethyl ester), mp 108°–109° C. (from toluene).

EXAMPLE 6

2-(Methoxyphenyl)-1-hydroxyethane-1,1-bis(phosphonic acid dimethyl ester) is reacted as described in Example 2, thus obtaining 2-(4-methoxyphenyl)-1-hydroxyethane-1,1-diphosphonic acid, mp 208°–209° C. (from acetonitrile).

EXAMPLE 7

4-Fluorophenylacetic acid chloride is reacted as disclosed in Example 1, producing 2-(4-fluorophenyl)-1-hydroxyethene-1-phosphonic acid dimethyl ester, mp 63° C. (from hexane/diisopropyl ether).

The thus-obtained product is reacted as described in Example 1, yielding 2-(4-fluorophenyl)-1-hydroxyethane-1,1-bis(phosphonic acid dimethyl ester), mp 129° C. (from diethyl ether).

EXAMPLE 8

2-(4-Fluorophenyl)-1-hydroxyethane-1,1-bis(phosphonic acid dimethyl ester) is reacted analogously to Example 2, thus producing 2-(4-fluorophenyl)-1-hydroxyethane-1,1-diphosphonic acid, mp 211°–213° C. (from isopropanol).

EXAMPLE 9

2-Fluorophenylacetic acid chloride is reacted as set forth in Example 1, yielding 2-(2-fluorophenyl)-1-hydroxyethene-1-phosphonic acid dimethyl ester, mp 71°–73° C. (from carbon tetrachloride/hexane).

The resultant product is reacted analogously to Example 1, thus obtaining 2-(2-fluorophenyl)-1-hydroxyethane-1,1-bis(phosphonic acid dimethyl ester), mp 146°–148° C. (from carbon tetrachloride/diisopropyl ether).

EXAMPLE 10

2-(2-Fluorophenyl)-1-hydroxyethane-1,1-bis(phosphonic acid dimethyl ester) is reacted analogously to Example 2, thus obtaining 2-(2-fluorophenyl)-1-hydroxyethane-1,1-diphosphonic acid, mp 218°–220° C. (from isopropanol).

EXAMPLE 11

2,6-Dichlorophenylacetic acid chloride is reacted as disclosed in Example 1 to obtain 2-(2,6-dichlorophenyl)-1-hydroxyethene-1-phosphonic acid dimethyl ester.

The resultant product is reacted according to Example 1, yielding 2-(2,6-dichlorophenyl)-1-hydroxyethane-1,1-bis(phosphonic acid dimethyl ester), mp 130°–132° C. (from toluene).

EXAMPLE 12

2-(2,6-Dichlorophenyl)-1-hydroxyethane-1,1-bis(phosphonic acid diemthyl ester) is reacted as described in EXample 2, yielding 2-(2,6-dichlorophenyl)-1-hydroxyethane-1,1-diphosphonic acid, mp 226°–228° C. (from isopropanol).

EXAMPLE 13

2-Thienylacetic acid chloride is reacted as disclosed in Example 1, thus obtaining 2-(2-thienyl)-1-hydroxyethene-1-phosphonic acid dimethyl ester, mp 148° C.

The resultant product is reacted under the conditions recited in Example 1 to the 2-(2-thienyl)-1-hydroxyethane-1,1-bis(phosphonic acid dimethyl ester).

EXAMPLE 14

2-(2-Thienyl)-1-hydroxyethane-1,1-bis(phosphonic acid dimethyl ester) is reacted as described in Example 2 to 2-(2-thienyl)-1-hydroxyethane-1,1-diphosphonic acid.

EXAMPLE 15

As described in Example 1, 2-naphthylacetic acid chloride is reacted to 2-(2-naphthyl)-1-hydroxyethene-1-phosphonic acid dimethyl ester, mp 120° C.

The thus-obtained product is reacted as described in Example 1, thus producing 2-(2-naphthyl)-1-hydroxyethane-1,1-bis(phosphonic acid dimethyl ester), mp 119° C.

EXAMPLE 16

2-(2-Naphthyl)-1-hydroxyethane-1,1-bis(phosphonic acid dimethyl ester) is reacted as set forth in Example 3, yielding 2-(2-naphthyl)-1-hydroxyethane-1,1-diphosphonic acid, mp 257° C.

EXAMPLE 17

1-Naphthylacetic acid chloride is reacted as described in Example 1 to 2-(1-naphthyl)-1-hydroxyethene-1-phosphonic acid dimethyl ester, mp 118° C.

The thus-obtained product is reacted analogously to Example 1 to 2-(1-naphthyl)-1-hydroxyethane-1,1-bis(phosphonic acid dimethyl ester), mp 146° C.

EXAMPLE 18

As disclosed in Example 3, 2-(1-naphthyl)-1-hydroxyethane-1,1-bis(phosphonic acid dimethyl ester) is reacted to 2-(1-naphthyl)-1-hydroxyethane-1,1-diphosphonic acid.

EXAMPLE 19

2-(4-Chlorophenylpropionic acid chloride is reacted as described in Example 1 to 2-(4-chlorophenyl)-1-hydroxypropene-1-phosphonic acid dimethyl ester.

The resultant product is reacted to 2-(4-chlorophenyl)-1-hydroxypropane-1,1-bis(phosphonic acid dimethyl ester.

EXAMPLE 20

As disclosed in Example 2, 2-(4-chlorophenyl)-1-hydroxypropane-1,1-bis(phosphonic acid dimethyl ester) is reacted to 2-(4-chlorophenyl)-1-hydroxypropane-1,1-diphosphonic acid.

EXAMPLE 21

Under the conditions described in Example 1, 3-chlorophenylacetic acid chloride is reacted to yield 2-(3-chlorophenyl)-1-hydroxyethene-1-phosphonic acid dimethyl ester, mp 136°–138° C. (from diethyl ether).

The thus-obtained product is reacted analogously to Example 1, yielding 2-(3-chlorophenyl)-1-hydroxyethane-1,1-bis(phosphonic acid dimethyl ester), mp 115°-116° C. (from hexane/diethyl ether).

EXAMPLE 22

2-(3-Chlorophenyl)-1-hydroxyethane-1,1-bis(phosphonic acid dimethyl ester) is reacted as described in Example 2, yielding 2-(3-chlorophenyl)-1-hydroxyethane-1,1-diphosphonic acid, mp 198°-200° C. (from isopropanol).

EXAMPLE 23

As described in Example 1, 4-tolylacetic acid chloride is reacted to yield 2-(4-tolyl)-1-hydroxyethenephosphonic acid dimethyl ester, mp 109°-111° C. (from diethyl ether).

The resultant product is reacted under the conditions of Example 1, thus obtaining 2-(4-tolyl)-1-hydroxyethane-1,1-bis(phosphonic acid dimethyl ester), mp 100°-102° C. (from diethyl ether).

EXAMPLE 24

2-(4-Tolyl)-1-hydroxyethane-1,1-bis(phosphonic acid dimethyl ester) is reacted as disclosed in Example 2, yielding 2-(4-tolyl)-1-hydroxyethane-1,1-diphosphonic acid, mp 211°-213° C. (from isopropanol).

EXAMPLE 25

A solution of 2.1 g of 2-(2-fluorophenyl)-1-hydroxyethane-1,1-diphosphonic acid in 30 ml of water is combined with a solution of 1.23 g of calcium acetate in 10 ml of water, and agitated for one hour at room temperature. The precipitate is then suctioned off, boiled with ethanol, dried, and the product is 2.82 g (96.3%) of 2-(2-fluorophenyl)-1-hydroxyethane-1,1-diphosphonic acid, calcium salt, mp above 350° C.

EXAMPLE 26

2-(4-Biphenyl)-1-hydroxyethane-1,1-bis(phosphonic acid dimethyl ester) is reacted with iodotrimethylsilane as disclosed in Example 2, and worked up, yielding 2-(4-biphenyl) 1-hydroxyethane-1,1-bisphosphonic acid, mp 218°-219° C. (isopropanol).

EXAMPLE 27

3-(4-Chlorophenyl)-1-oxopropane-1-phosphonic Acid Dimethyl Ester (a) At 0° C., a solution of 3.6 g of trimethyl phosphite in 10 ml of diethyl ether is added dropwise to a solution of 5.1 g of 3-(4-chlorophenyl)propionic acid chloride in 25 ml of diethyl ether. The mixture is first stirred for 2.5 hours at 0° C., then another 2 hours at room temperature. After concentration of the solution, the residue is distilled with the use of a bulb tube at 200°-205° C. and a pressure of 0.02 mm, yielding 5.2 g (74%) of 3-(4-chlorophenyl)-1-oxopropane-1-phosphonic acid dimethyl ester.

3-(4-Chlorophenyl)-1-hydroxypropane-1,1-bis(phosphonic Acid Dimethyl Ester)

(b) Under agitation at 0° C., a solution of 4.7 g of 3-(4-chlorophenyl)-1-oxopropane-1-phosphonic acid dimethyl ester in 15 ml of diethyl ether is added dropwise to a solution of 2.1 g of dimethyl phosphite and 0.1 g of diethylamine in 15 ml of diethyl ether. The mixture is agitated for 30 minutes, the precipitate is vacuum-filtered and washed with diethyl ether, yielding 5.6 g (84%) of 3-(4-chlorophenyl)-1-hydroxypropane-1,1-bis(phosphonic acid dimethyl ester), mp 112° C.

EXAMPLE 28

3-(4-Chlorophenyl)-1-hydroxypropane-1,1-diphosphonic Acid 2.7 g of 3-(4-chlorophenyl)-1-hydroxypropane-1,1-bis(phosphonic acid dimethyl ester) is combined with 17 ml of concentrated hydrochloric acid and heated for 3 hours to 100° C. After cooling, the crystallized product is vacuum-filtered and recrystallized from isopropanol, thus obtaining 1.62 g (70%) of 3-(4-chlorophenyl)-1-hydroxypropane-1,1-diphosphonic acid, mp 201° C.

The following compounds are prepared analogously to Example 1:

EXAMPLE 29

(a) 3-(4-Isopropylphenyl)-1-oxopropane-1-phosphonic Acid Dimethyl Ester
(distilled in a bulb tube at 1 mm, 230°-240° C. furnace temperature)
and therefrom:
(b) 1-Hydroxy-3-(4-isopropylphenyl)propane-1,1-bis(phosphonic Acid Dimethyl Ester)
mp 79° C. (hexane).

EXAMPLE 30

(a) 3-(3,4-Dichlorophenyl)-1-oxopropane-1-phosphonic Acid Dimethyl Ester
(distilled in a bulb tube at 0.03 mm, 234°-240° C. furnace temperature)
and therefrom:
(b) 3-(3,4-Dichlorophenyl)-1-hydroxypropane-1,1-bis(phosphonic Acid Dimethyl Ester)
mp 120° C. (hexane/diethyl ether).

EXAMPLE 31

(a) 4-(4-Chlorophenyl)-1-oxobutane-1-phosphonic Acid Dimethyl Ester
(distilled in a bulb tube at 0.02 mm, 225° C. furnace temperature)
and therefrom:
(b) 4-(4-Chlorophenyl)-1-hydroxybutane-1,1-bis(phosphonic Acid Dimethyl Ester)
mp 75° C. (hexane/diethyl ether).

The following compounds are prepared analogously to Example 2:

EXAMPLE 32

1-Hydroxy-3-(4-isopropylphenyl)propane-1,1-diphosphonic Acid mp 174° C. (isopropanol).

EXAMPLE 33

3-(3,4-Dichlorophenyl)-1-hydroxypropane-1,1-diphosphonic Acid mp 187° C. (isopropanol).

EXAMPLE 34

4-(4-Chlorophenyl)-1-hydroxybutane-1,1-diphosphonic Acid mp 181° C. (isopropanol).

The preceding examples can be repeated with similar success by substituting the generically or specifically described reactants and/or operating conditions of this invention for those used in the preceding examples.

From the foregoing description, one skilled in the art can easily ascertain the essential characterisitics of this invention, and without departing from the spirit and scope thereof, can make various changes and modifications of the invention to adapt it to various usages and conditions.

What is claimed is:

1. A pharmaceutical composition comprising an antiinflammatorily effective amount of a diphosphonic acid derivative of the formula $$Ar-(CH_2)_n-CH-\underset{\underset{PO(OR^2)_2}{|}}{\overset{\overset{PO(OR^2)_2}{|}}{\underset{|}{C}}}-OH$$
$$\overset{R^1}{|}$$

wherein
n is 0, 1 or 2;
$R^1$ is hydrogen or alkyl or 1–4 carbon atoms;
$R^2$ is hydrogen, an alkali metal atom, an alkaline earth metal atom, or alkyl or 1–4 carbon atoms; and
Ar is phenyl; phenyl substituted by fluorine, chlorine, alkyl of 1–4 carbon atoms, or alkoxy of 1–4 carbon atoms; naphthyl; biphenyl; or thienyl;
or when $R^2$ is H, a physiologically acceptable salt thereof with an organic base
and a pharmacologically acceptable adjuvant.

2. A composition of claim 1, wherein the diphosphonic acid derivative is 3-(4-chlorophenyl)-1-hydroxypropane-1,1-bis(phosphonic acid dimethyl ester), or 3-(4-chlorophenyl)-1-hydroxypropane-1,1-diphosphonic acid.

3. A composition of claim 1, wherein the diphosphonic acid derivative is 1-hydroxy-3-(4-isopropylphenyl)-propane-1,1-bis(phosphonic acid dimethyl ester), or 1-hydroxy-3-(4-isopropylphenyl)propane-1,1-diphosphonic acid.

4. A composition of claim 1, wherein the diphosphonic acid derivative is 3-(3,4-dichlorophenyl)-1-hydroxypropane-1,1-bis(phosphonic acid dimethyl ester), or 3-(3,4-dichlorophenyl)-1-hydroxypropane-1,1-diphosphonic acid.

5. A composition of claim 1, wherein the diphosphonic acid derivative is 4-(4-chlorophenyl)-1-hydroxybutane-1,1-bis(phosphonic acid dimethyl ester), or 4-(4-chlorophenyl)-1-hydroxybutane-1,1-diphosphonic acid.

6. A composition of claim 1, wherein the diphosphonic acid derivative is 2-(4-chlorophenyl)-1-hydroxyethane-1,1-bis(phosphonic acid dimethyl ester), or 2-(4-chlorophenyl)-1-hyroxyethane-1,1-diphosphonic acid.

7. A composition of claim 1, wherein the diphosphonic acid derivative is 2-(4-biphenyl)-1-hydroxyethane-1,1-bis-(phosphonic acid dimethyl ester), or 2-biphenyl-1-hydroxyethane-1,1-diphosphonic acid.

8. A composition of claim 1, wherein the diphosphonic acid derivative is 2-(4-methoxyphenyl)-1-hydroxyethane-1,1-bis(phosphonic acid dimethyl ester), or 2-(4-methoxyphenyl)-1-hydroxyethane-1,1-diphosphonic acid.

9. A composition of claim 1, wherein the diphosphonic acid derivative is 2-(4-fluorophenyl)-1-hydroxyethane-1,1-bis(phosphonic acid dimethyl ester), 2-(4-fluorophenyl)-1-hydroxyethane-1,1-diphosphonic acid, or the calcium salt thereof.

10. A composition of claim 1, wherein the diphosphonic acid derivative is 2-(2-fluorophenyl)-1-hydroxyethane-1,1-bis(phosphonic acid dimethyl ester), or 2-(2-fluorophenyl-1,-hydroxyethane-1,1-diphosphonic acid.

11. A composition of claim 1, wherein the diphosphonic acid derivative is 2-(2,6-dichlorophenyl)-1-hydroxyethane-1,1-bis(phosphonic acid dimethyl ester), or 2-(2,6-dichlorophenyl)-1-hydroxyethane-1,1-diphosphonic acid.

12. A composition of claim 1, wherein the diphosphonic acid derivative is 2-(2-thienyl)-1-hydroxyethane-1,1-bis(phosphonic acid dimethyl ester), or 2-(2-thienyl)-1-hydroxyethane-1,1-diphosphonic acid.

13. A composition of claim 1, wherein the diphosphonic acid derivative is 2-(2-naphthyl)-1-hydroxyethane-1,1-bis(phosphonic acid dimethyl ester), or 2-(2-naphthyl)-1-hydroxyethane-1,1-diphosphonic acid.

14. A composition of claim 1, wherein the diphosphonic acid derivative is 2-(1-naphthyl)-1-hydroxyethane-1,1-bis(phosphonic acid dimethyl ester), or 2-(1-naphthyl)-1-hydroxyethane-1,1-diphosphonic acid.

15. A composition of claim 1, wherein the diphosphonic acid derivative is 2-(4-chlorophenyl)-1-hydroxypropane-1,1-bis(phosphonic acid dimethyl ester), or 2-(4-chlorophenyl)-1-hydroxypropane-1,1-diphosphonic acid.

16. A composition of claim 1, wherein the diphosphonic acid derivative is 2-(3-chlorophenyl)-1-hydroxyethane-1,1-bis(phosphonic acid dimethyl ester), or 2-(3-chlorophenyl)-1-hydroxyethane-1,1-diphosphonic acid.

17. A composition of claim 1, wherein the diphosphonic acid derivative is 2-(4-tolyl)-1-hydroxyethane-1,1-bis(phosphonic acid dimethyl ester), or 2-(4-tolyl)-1-hydroxyethane-1,1-diphosphonic acid.

18. A method of treating inflammation in a patient in need of such treatment comprising administering to the patient an antiinflammatorily effective amount of a diphosphonic acid derivative of the formula $$Ar-(CH_2)_n-CH-\underset{\underset{PO(OR^2)_2}{|}}{\overset{\overset{PO(OR^2)_2}{|}}{\underset{|}{C}}}-OH$$
$$\overset{R^1}{|}$$

wherein
n is 0, 1 or 2;
$R^1$ is hydrogen or alkyl or 1–4 carbon atoms;
$R^2$ is hydrogen, an alkali metal atom, an alkaline earth metal atom, or alkyl or 1–4 carbon atoms; and
Ar is phenyl; phenyl substituted by fluorine, chlorine, alkyl of 1–4 carbon atoms, or alkoxy of 1–4 carbon atoms; naphthyl; biphenyl; or thienyl;
or when $R^2$ is H, a physiologically acceptable salt thereof with an organic base.

19. A method of claim 18 wherein the patient is suffering from arthritis.

20. A composition of claim 1, wherein the amount of diphosphonic acid derivative is 10–500 mg.

21. A method of claim 18, wherein the daily dosage of the diphosphonic acid derivative is 1–50 mg/kg of body weight.

* * * * *